United States Patent [19]

Platt

[11] Patent Number: 4,910,151

[45] Date of Patent: Mar. 20, 1990

[54] SAMPLE MONITORING INSTRUMENT FOR ON-LINE APPLICATION

[75] Inventor: Moses Platt, Reading, Mass.

[73] Assignee: Tytronics, Incorporated, Waltham, Mass.

[21] Appl. No.: 38,221

[22] Filed: Apr. 14, 1987

Related U.S. Application Data

[62] Division of Ser. No. 904,197, Sep. 5, 1986.

[30] Foreign Application Priority Data

Sep. 6, 1985 [GB] United Kingdom ............. 8522126

[51] Int. Cl.⁴ ............................................ G01N 31/16
[52] U.S. Cl. .................................. 436/163; 436/51; 436/52; 436/54; 436/55; 422/81; 137/143; 73/226; 366/191
[58] Field of Search .................. 436/52, 163, 54, 55, 436/180.51; 422/68, 81; 137/130, 132, 143, 145, 152; 366/191; 73/226

[56] References Cited

U.S. PATENT DOCUMENTS

| | | | |
|---|---|---|---|
| 618,835 | 2/1899 | Bowen | 137/145 |
| 1,235,316 | 7/1917 | Henderson | 137/145 |
| 1,564,430 | 12/1925 | Maddrell | 137/130 |
| 1,574,149 | 2/1926 | Hompes et al. | 137/145 |
| 2,461,334 | 2/1949 | Major | 210/17 |
| 2,884,942 | 5/1959 | Caldwell et al. | 137/132 |
| 3,415,267 | 12/1968 | Karlen et al. | 137/132 |
| 3,589,385 | 6/1971 | Vitous | 137/145 |

FOREIGN PATENT DOCUMENTS

| | | |
|---|---|---|
| 453989 | 6/1973 | Australia . |
| 2127244 | 11/1972 | Fed. Rep. of Germany . |
| 2506453 | 11/1982 | France . |

OTHER PUBLICATIONS

Soviet Inventors Illustrated, Section Chemistry, Week C27, Aug. 13, 1980 (SU 491286, No. 17, 1979).
Process Instruments and Controls Handbook, Third Edition, pp. 6.98–6.104.

Primary Examiner—Barry S. Richman
Assistant Examiner—Lynn M. Kummert

[57] ABSTRACT

An apparatus and method for on-line monitoring of a characteristic of a process liquid stream includes a cell for isolating a precise volume of the liquid. A sample chamber is over filled and the excess removed from the chamber by using a downwardly extending drain line which terminates at a precisely positioned, downwardly facing inlet negative pressure is applied to the drain line to draw the excess liquid upwardly from the captured volume until the liquid level reaches the inlet and entry of air disrupts the liquid draining effect. The embodiment shown employs a closed volume, a vent, a conduit for delivery of process liquid into the cell under pressure and a syphon/drain line for removing excess liquid from the cell volume until there remains only a sample of accurately repeatable volume.

2 Claims, 5 Drawing Sheets

SAMPLE MONITORING INSTRUMENT FOR ON-LINE APPLICATION

This is a divisional of application Ser. No. 904,197, filed Sept. 5, 1986.

This invention relates generally to on-line process instruments or systems for monitoring the composition of liquid media in a process plant. More particularly, the invention consists of a sampling/reaction assembly to function as the central component of on-line instrumentation, in which a liquid sample is captured and measurement of a characteristic, e.g., ionic content, is made, usually after a chemical reaction occurs.

Process instruments are used to perform chemical analyses in multi-stage processes to ensure product quality is maintained and to save energy and raw material. These benefits result from operating within closer tolerances and from the quicker corrective response to inefficient conditions. Process instrument hardware for evaluation of liquid media is typically divided into two general categories based, in part, on whether the sampling of an accurate volume of liquid is important in the measurement process and whether the sample is conditioned. Instruments directly in the process stream, i.e., "in-line", do not condition the sample, nor do they need an accurate volume of sample for testing since they are always subject to the same flow cross-section of liquid. The information supplied by these instruments is continuous, but precision and accuracy are low. Examples of such types of instruments are pH electrodes, ion-selective electrodes, oxidation-reduction potential electrodes, and specific gravity and conductivity instruments.

The second category of instruments consists typically of laboratory-type equipment ruggedized for industrial application. In these special process instruments, often referred to as "on-line", the liquid sample is removed from the process stream, conditioned to standard test conditions by reducing pressure and temperature, filtered to remove contaminants and solids, transferred as a known volume to a second cell in the instrument and reacted with chemicals prior to measurement of a specific component or characteristic. The data from this type of instrument is discrete, being obtained at intervals of from one to twenty minutes, with precision and accuracy comparable to that obtained in a chemical laboratory. The need to make operation automatic and the hardware particularly rugged are the significant differences from instruments designed solely for laboratory use, but these instruments still require a sophisticated operator in order to obtain proper test results. Examples of this type of instrument are titrators and colourimeters.

Objectives of the present invention include: to provide an on-line instrument capable of capturing a liquid sample from a process stream for measurement of a characteristic with high repeatability; to provide an on-line instrument capable of precision, accuracy and reliability without complex interconnected assemblies and delicate precision parts typical of laboratory-type on line instruments; and to provide an on-line instrument capable of reliable operation while interfacing with process environments with difficult conditions of temperature, chemical composition or contamination.

SUMMARY OF THE INVENTION

According to the invention it is realized that increase in precision of repeatedly capturing a small volume of liquid can be achieved by employing a downwardly directed drain inlet precisely located at the desired liquid level of a chamber and applying pressure conditions to cause flow of excess liquid upwardly from the captured volume until the liquid level reaches the inlet and entry of air disrupts the liquid-transfer effect. It is found that, by establishing the level in this way, the wettability of the substance defining the inlet does not substantially affect the accuracy of the level achieved, hence an unusually accurate volume can be repeatedly achieved, despite differences in the character of the liquid from one sample to another. In the case of a 10 ml sample, accuracies of 1% repeatability can be achieved, in which 1% may represent only one small drop.

According to one aspect of the invention described, a sampling cell assembly comprises: a sampling cell defining a closed volume, example inlet conduit means for delivering a pressurized flow of process liquid into the cell, vent mens for flow of vent gas through the cell, vent valve means for controlling flow of vent gas through the cell, a siphon/drain conduit means having a first end downwardly disposed within the closed volume of the cell with the inlet of the first end at a predetermined point within the cell and a second end downwardly disposed outside the cell with the outlet from the second end disposed a predetermined distance below the inlet, whereby, by timely operation of the vent valve, an excess volume of sample liquid delivered into the cell via the sample inlet conduit means is removed by siphon action through the siphon/drain conduit means until there remains in the cell only a repeatable volume of sample liquid.

In preferred embodiments, the assembly further includes titrant inlet conduit means for delivery of titrant liquid into the cell; the cell assembly further comprises a manifold defining a plurality of orifices for introduction into the cell of sensor means for determining a characteristic of the sample liquid; the assembly further includes inlet conduit means for delivery of calibrating liquid into the cell; and the assembly further includes inlet conduit means for delivery of reagent into the cell.

According to another aspect of the invention, a method for on-line determination of a characteristic of a liquid process stream comprises providing a sample cell of closed volume, sample inlet conduit means for delivery of a flow of process liquid into the cell, vent means for flow of vent gas through the cell, vent valve means for controlling flow of vent gas through the cell, siphon/drain conduit means having a first end downwardly disposed within the closed volume of the cell with the inlet of the first end at a predetermined point within the closed volume of the cell and a second end downwardly disposed outside the cell with the outlet from the second end disposed at a predetermined distance below the inlet, with the vent valve mean open, causing a pressurized flow of process liquid through the sample conduit means into the cell volume, after a volume of sample liquid sufficient to raise the level of liquid in the cell above the inlet end of the siphon/drain conduit is collected within the cell, closing the vent valve means, continuing to flow pressurized liquid into the cell volume via the sample inlet conduit means to establish flow of excess fluid through te drain/siphon conduit means out the cell volume, ceasing all flow through the sample inlet conduit means, opening the vent valve means to create siphoning flow through the siphon/drain conduit means to drain excess liquid from the cell volume, the siphoning flow ceasing automatically when the level of sample liquid in the cell volume reaches the level of the inlet end, there remaining, in the cell volume, a sample of repeatable volume, and testing the remaining sample liquid for a characteristic desired to be known.

In preferred embodiments, the method further comprises delivering into the cell volume a measured volume of liquid for reaction with a component of the sample volume for the purpose of determining the characteristic; and the liquid is titrant or a reagent.

The present invention is particularly directed to an improved arrangement of hardware for removing a sample from the process stream, capturing a precise repeatable volume of the sample liquid and allowing a controlled chemical reaction to occur involving the sample in the same hardware prior to measurements being made on the reacted sample. The design of the device to be ssed according to the present invention eliminates the need for: (1) accurate and precise sample metering pumps; or (2) valving arrangements or other complex fluid handling equipment to capture a precise volume of the sample. The invention uses a very simple arrangement of a partially pressurized cell and a gravity activated siphon and so is a relatively simple system lacking parts which are prone to failure when in contact with a sample stream.

In preferred practice, the parts that are included in the instrument of the present invention include: (1) means for on-line sampling of the process stream in a volumetrically precise and repeatable manner at predetermined intervals; (2) means for introducing reagents to the reaction cell to condition the sample; (3) means for introducing a titrant relevant to the measurement to be made to the reaction cell; and (4) means for introducing a calibrant into the reaction cell in place of the sample in a volumetrically precise and repeatable manner such that it can be analyzed to correct for changes in the measuring instrument and this assembly.

PREFERRED EMBODIMENT

For a better understanding of the invention and to show how the same can be carried into effect, reference will now be made, by way of example only, to the accompanying drawings, wherein:

FIGS. 1a to 1c are elevations of sides at right angles to each other viewed in turn of an assembled sampling reaction cell/manifold for a device embodying this invention, with all parts in place;

Referring now to the drawings, FIGS. 1a to 1c show an on-line wet chemical analyzer consisting of a complete sampling/reaction assembly as it would exist in an on-line process installation. The attachment of plumbing lines and tubing to the plurality of connections for introduction of fluids would be all that would be needed to make it ready for use. As shown, a manifold block 1 is the junction point for a plurality of connections for flows of fluid including sample inlet connection 7, siphon/waste connection 6, air vent connection 5, titran connection 14, standard or calibrant connection 12, and reagent connection 13. Secured to the manifold block through the use of clamp knobs 4 and clamp rods 8 is a sampling reaction cell 2. A plurality of orifices in the manifold block 1 is provided for installing ion sensing probes 9, temperature sensing probes 10, and conductivity sensing probes 11. A clamp plate 3 is used to compress seals 19 (see FIG. 2) around the previously described probes 9, 10 and 11 to prevent leakage of liquids or air.

Figure 2:
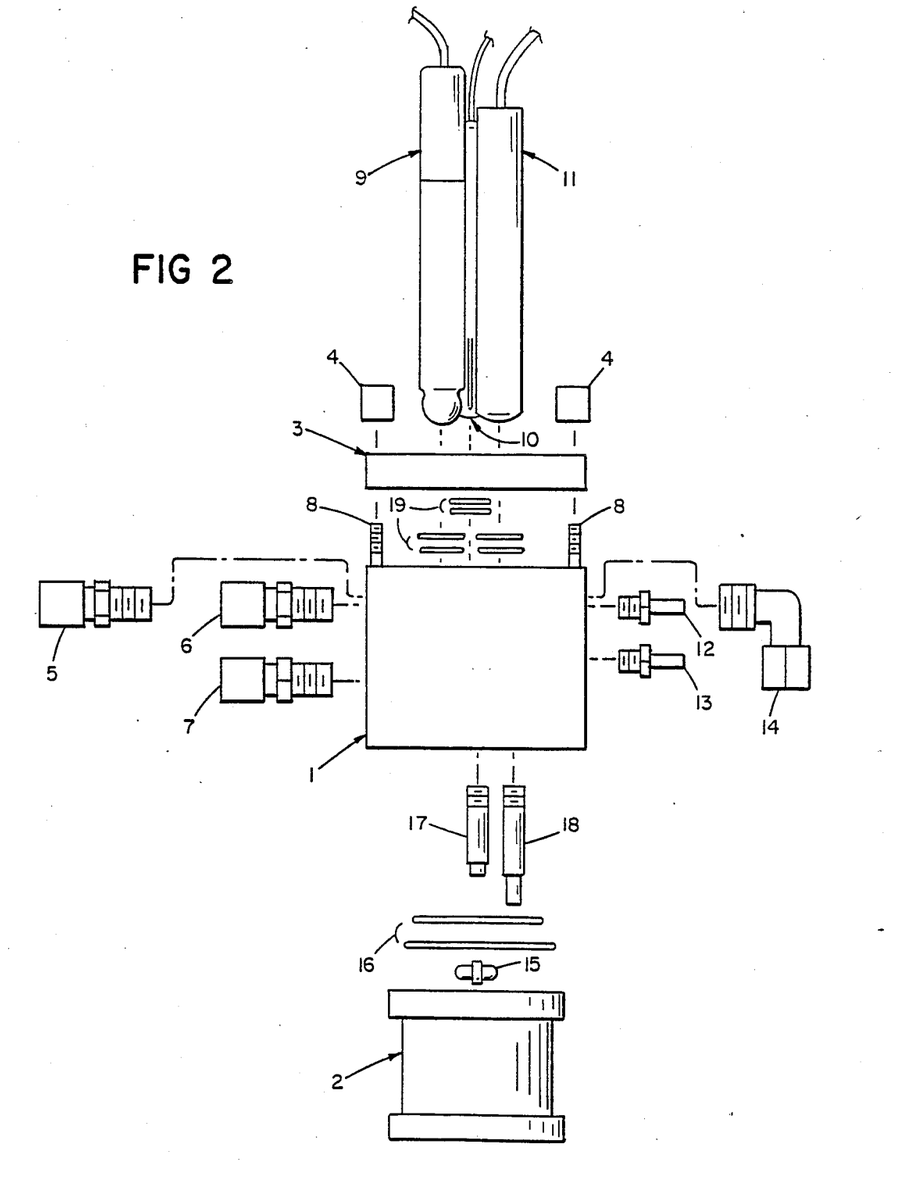
FIG. 2 is an exploded view of the sampling/reaction cell/manifold combination of FIGS. 1a to 1c with all relevant parts shown.

In FIG. 2, the remaining parts of the assembly are pictured, including the aforementioned seals 19, additional seals 16, to prevent leakage of liquids or air between the cell 2 and manifold 1, a magnetic stir bar 15 to agitate the captured sample during reaction or measurement, a drain/siphon fitting 17 used to establish the gravity siphon and leave a precise volume of sample in the cell and a titrant fitting 18 to introduce titrant required for the measurement. All of the items described are constructed of materials inert to the sample stream and which are such as to minimize deterioration and clogging and increase service life and reliability.

The operation of this arrangement, which preferably is performed by a CPU microprocessor programmed for the task, is as follows, with reference to FIGS. 3 and 3a through 3h.

Figure 3:
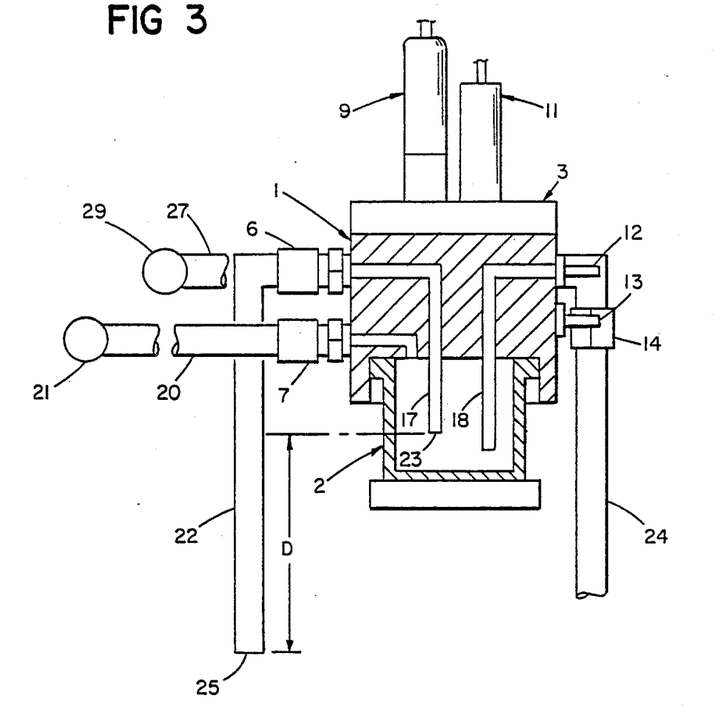
FIG. 3 is a side elevation, taken in section, of the assembled sampling reaction cell/manifold of the invention.

In FIG. 3, cell 2 and manifold 1 are shown in section, with siphon/waste fitting 17 and titrant fitting 18 extending into the cell. Sample inlet piping 20 extends from a process stream connection (not shown), through valve 21, to sample inlet fitting 7. Siphon/drain piping 22 extends from siphon/waste connection 6, to a distance, D, below the inlet opening to siphon/waste fiting 17 within the cell, D, being elected to establish a pressure differential between the inlet 23 of siphon/drain fitting 17 and the outlet 25 of siphon/drain piping 22 sufficient to start and maintain gravity siphon flow, as will be described below, e.g., a pressure differential of about 6 inches of water. Titrant piping 24 delivers titrating fluid from a source, through a metering pump, and into the cell via titrant connection 14 and fitting 18. The vent line from the cell to fitting 5 (FIG. 1a) lies behind the siphon/drain line and is omitted for clarity. The vent line terminates in vent piping 27 and valve 29, which may be level, as shown, or elevated. The internal lines from sandard and reagent fittings 12, 13, and the internal components of probes and sensors 9, 11 are also omitted for clarity.

Figure 3A:
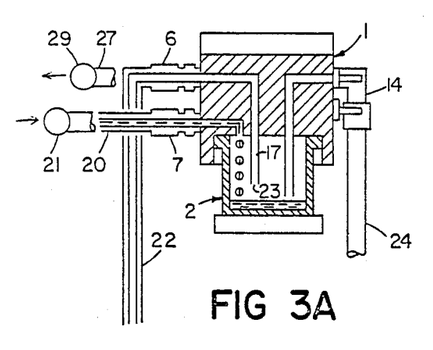
FIGS. 3a through 3h are sequential side elevations, taken in settion, of the sample capture process of the invention.
Figure 3B:
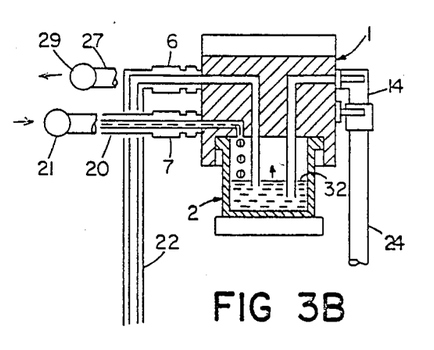

Referring to FIG. 3a, with the vent valve 29 open, typically to the atmosphere, the sample valve 21 is opened, causing pressurized sample 30 to flow via inlet piping 20 from the liquid process stream. The vent valve 29 is kept open as sample 30 fills the cell from the bottom, displacing entrapped air through the vent piping 27 and valve 29, and also through the siphon/waste piping 22, until the cell is about half full, with the liquid level 32 above the inlet end 23 of the siphon/waste fitting 17 (FIG. 3b). This is typically determined by time, based on the volume flow rate through sample inlet piping 20, as programmed into the CPU microprocessor by operating personnel.

Figure 3C:
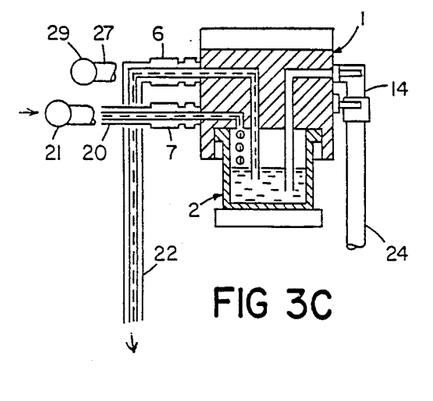
Figure 3D:
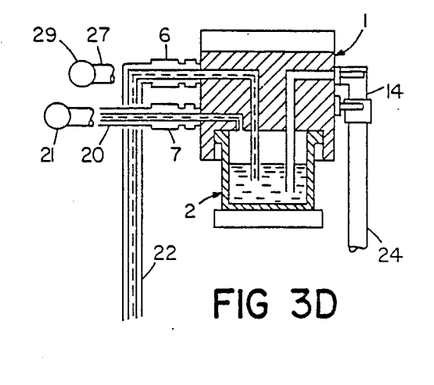

The vent valve 29 is then closed as pressurized sample continues to flow through inlet piping 20 into cell 2. As the cell volume is now closed, excess sample 30 is forced to flow out of the cell through siphon/drain piping 22 (FIG. 3c). After the siphon/drain piping is filled, the sample valve 21 is closed to stop flow of sample into the cell. The air vent valve 29 is also in closed position at this point, so all flow is stopped (FIG. 3d).

Figure 3E:
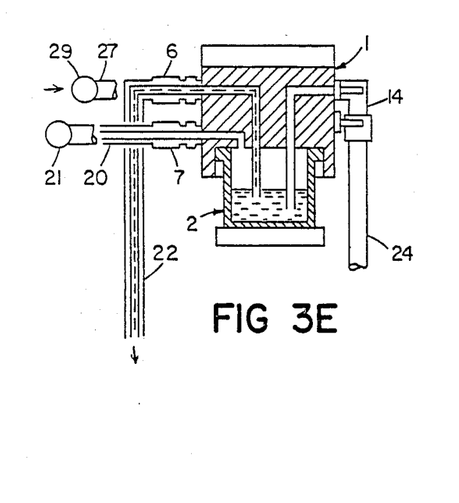
Figure 3F:
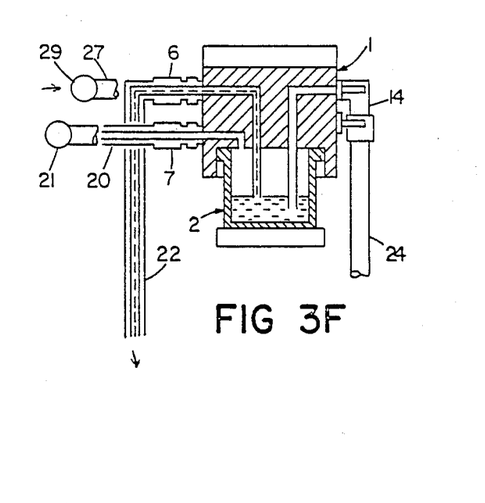
Figure 3G:
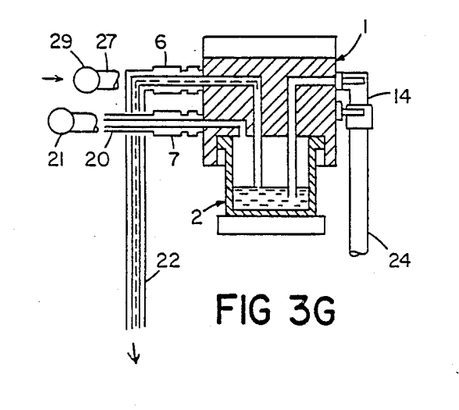
Figure 3H:
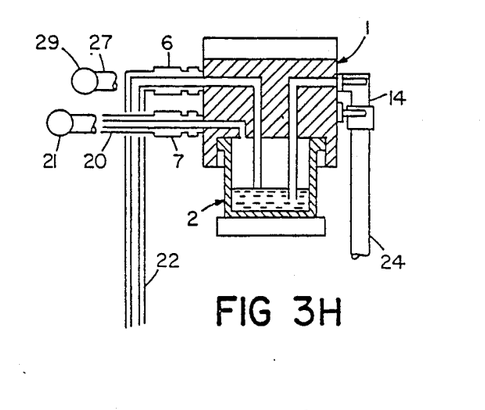

The air vent valve 29 is then reopened, allowing flow of the sample liquid held in the siphon/drain fitting 17 and piping 22 (FIG. 3e). The gravity siphon action continues until the liquid level 32 of sample in cell 2 falls below the inlet end 23 of siphon/waste fitting 17, opening the inlet end of the tube to air in the cell, breaking siphon and leaving a precisely repeatable volume of sample liquid remaining in the cell (FIG. 3f).

The open air vent valve and exposed inlet end of the siphon/drain line in the cell allow the drain line to empty (FIG. 3g), leaving a captured sample of liquid of volume repeatable, e.g., within $\pm\frac{1}{2}\%$, from sample to sample. (The volume of cell 2 and the sample volume captured are selected on the basis of the process to be monitored, and the nature of the testing to be performed. For example, the cell volume may be 40 ml, and the captured sample volume 20 ml, or the cell volume may be 70 ml, and the captured sample volume 8 ml, e.g., where the process liquid is concentrated, and relatively larger volumes of additives are required.)

At this point, depending on the characteristic or component to be determined and the test to be performed, a measured volume, accurate to about $\pm 1\%$ with a standard titrant pump, of titrant or reagent, or both, are added into the cell. A chemical reaction may be induced, and the desired characteristic or component measured, typically for variation from a standard.

In the process sequence described above, the cell was shown as initially empty. Typically, however, the reacted sample liquid from the previous cycle must be purged form the cell before the next sample is taken. Due to the addition of titrant during testing of the previous sample, the liquid level in the cell is above the inlet of the siphon/drain fitting, e.g., in a system for capturing a sample volume of 8 m, the final test volume in the cell may be 40 to 50 ml. Flow of liquid through the siphon/drain conduit is established by opening the sample inlet valve 21 with the vent valve 29 closed. Vent valve 29 is thenoopened and sample inlet valve 21 is closed. Gravity siphon flow through the siphon drain fitting 17 and piping 22 continues until only the capture volume remains in the cell. The condition established i FIG. 3c is maintained to statistically purge the volume of sample remaining in the cell, e.g., six to eight volume exchanges are typically sufficient to provide a captured sample that is better than 95% clean.

At appropriate intervals, e.g., after a redetermined number of process samples are run, a calibrating liquid is allowed to flow into cell 2. The calibrating liquid is captured in the same manner as the volume of sample described above. The addition of reagent or titrant is carried out in the same manner. Measurement of the calibrating liquid characteristic or component allows for recalibration of the electrodes, sensors and probes to correct for change in the system, as typically will occur over time. It also allows the operator to compare on-line process readings with a periodic reading on a sample of known characteristic. Examples of processes where this is of particular value include:

Steady-state processes, such as maintenance of peroxide at optimum concentration in cotton fabric bleaching. As peroxide is continuously added (solution addition) and depleted (in bleaching action), the concentration changes over a fairly narrow range. At too high a concentration of peroxide, the fabric is damaged, and at too low a concentration, the fabric is inadequately treated. A sample taken at the optimum concentration, prepared to ease sample handling (e.g. filtered), provides a good calibrating solution.

Depletion processes, such as plating copper onto inert medium in the manufacture of printed circuit boards. In this process, the copper concentration is constantly decreasing as the copper is deposited on the board. Monitoring can help prevent excessively low concentrations of copper, which result in unacceptably uneven coverage For this process,, an exact sample of the plating bath, including interfering additives, under conditions slightly above the minimum copper concentration situation gives maximum precision (through standardization) at the critical end of the process range, when additional copper mutt be added to the bath.

Saturation processes, such as waste treatment in which copper ions in solution are precipitated out to prevent their discharge to the general environment. Typically, a chemical is added to cause this to occur, based on an assumed inflow of copper ions. During high-inflow periods, the solution can become overloaded with copper, requiring addition of greater amounts of the treating chemical A calibrating liquid near this upper limit gives maximum precision.

By way of example only, one specific testing procedure will now be described.

EXAMPLE

Caustic scrubber, e.g., sodium hydroxide, is pumped from a batch holding tank through pipes in petrochemical plants to remove, i.e., "scrub", dangerous chemicals leaking from pipe valves and fittings. The concentration of caustic solution in the batch tank is monitored to ensure effective and efficient maintenance of a safe operating environment within the plant.

As scrubbing proceeds, the concentration of the caustic solution is reduced due to the intended chemical reaction of the caustic with chemicals in the pipes and the dissolution of additional scrubbed chemicals. The initial concentration of the NaOH is about 20 percent and the operation continues until the NaOH becomes ineffective at some low concentration, e.g., about 2-5 percent. The process is then stopped and the holding tank is replenished with fresh solution. Since scrubbing is carried out continuously, a second holding tank is kept ready for use when the first tank is being recharged.

The concentration of the caustic solution is analyzed by simple acid-based analysis to an endpoint, as sensed by a pH electrode, using the on-line wet chemical analyzer of the invention, as will now be described. With vent valve 29 open, sample valve 21 is opened allowing NaOH to flow through sample inlet piping 20 into the volume of cell 2. After a predetermined time, programmed into the associated CPU microprocessor, when the liquid level in the cell is aove the inlet end 23 of siphon/drain fitting 17, vent valve 29 is closed to cause flow of liquid through fitting 17 and siphon/drain piping 22. After a volume of flow calculated to flush the previous sample from the cell and provide a new sample of desired cleanliness, e.g., 160 ml., sample inlet valve 21 is losed and all flow stops.

Vent valve 29 is opened and excess sample fluid flows through siphon/drain piping 22 and fitting 17 from the volume of cell 2 by gravity siphon action until the level of liquid in the cell drops below the inlet end 23 of fitting 17, at which point siphon is interrupted, and the liquid in fitting 17 and siphon/drain piping 22 empties from outlet 25.

There remains within the cell a captured sample of repeatable volume, e.g., 8 ml., for analysis. To the captured sample there is added, via reagent connection 12, 20 ml of barium chloride to counteract the presence of carbonate, usually found in the scuubber solution, which interferes with the acid-based titration analysis of the sample. A titrate of 3N (Normal) hydrochloric acid (HCl) is metered into the cell via titrant piping 24, connection 14 and fitting 18, within the cell, until the predetermined electrochemical potential, i.e., endpoint, of the reaction is reached.

The CPU microprocessor derives the concentration of the NaOH caustic solution and stores the result, as well as sending the result to process display or recorder devices via any of several standard industrial signal devices.

The analysis is thus fully automated and can be repeated on a frequency programmed by the operator.

The arrangement of this invention is further of use, for example, in the power and utility industry, pulp and paper, food and beverage and chemical/petrochemical industries as well as in the petroleum, plating, dairying, rubber and plastics, primary metals, stone, clay and glass, textile and pharmaceutical industries; in fact, in any industry involving use of liquid media whose composition it is important to monitor in order to determine if a process liquid is used, depleted or changed in composition during an industrial process and/or when it is discharged to the environment.

The arrangement of the present invention may be used, more specifically, for example, in analyses using sensing probes to monitor composition of liquids. The siphon action of the arrangement may also be modified to capture precise sizes of sample for use in instruments where other sensing methods are employed and the applicability of the present invention is independent of the sensing technology used. These methods may include, but are not limited to, amperometric, colourimetric and spectrophotometric methods. The arrangement may be used to condition and/or dilute a sample before analysis, as well as oo ensure precision of sample volume.

Other embodiments are within the following claims, for example, the vent may be connected to a source of inert or other gas, rather than being open to the atmosphere, or the vent may be pressurized and the system operated at superatmospheric pressure. The system may include liquid flow and liquid level sensors for controlling operation of valves, and a dump valve may be provided at the bottom of the cell for ease in purging.

What is claimed is:

1. In a method for determination of a characteristic of a liquid process stream by wet chemical analysis to enable control of said process, comprising the steps of (a) defining a predetermined volume of sample to be analyzed and (b) performing said wet chemical analysis on said sample by progressively adding to said sample a measured flow of liquid reagent to cause progressive reaction with said sample while sensing a parameter of the liquid sample as said reaction with said reagent proceeds, the improvement wherein said step (a) of defining said volume of sample to be analyzed comprises providing a siphon cell having a closed volume, sample inlet conduit means for delivery of a flow of process liquid into said cell, vent means for flow of vent gas into said cell, and siphon/drain conduit means having an inlet and an outlet, said conduit means having a first end defining said inlet downwardly disposed within the volume of said cell with said inlet at a predetermined level spaced from the bottom and top of said cell, the partial volume of said cell below said inlet sized to define a predetermined volume of sample to be analyzed, and the partial volume of aid cell above the level of the inlet enabling additional liquid to be introduced into said cell in the performance of said method, and said conduit means having a second end defining said outlet downwardly disposed outside said cell with said outlet disposed at a predetermined distance below said inlet, causing a flow of process liquid through said sample inlet conduit means into said cell to collect a sample in said cell and establish a level of liquid in said cell above the inlet of said siphon/drain conduit means, continuing to cause flow of said liquid into said volume via said sample inlet conduit means to establish flow of excess process liquid out of said cell volume through said drain/siphon conduit means, filling said drain/siphon conduit, after said drain/siphon conduit is filled, ceasing all flow through said sample inlet conduit means and creating siphoning flow through said siphon/drain conduct means to drain excess process liquid from said cell, said siphoning flow ceasing automatically when the level of process liquid in said cell volume reaches the level of said inlet end of said siphon/drain conduit, thereby defining, in said cell, a sample of predetermined repeatable volume, and conducting said step (b) of performing said wet chemical analysis in situ within said siphon cell comprising, by titrating techniques, proressively delivering into said syphon cell a measured flow of liquid reagent to cause progressive reaction with said sample in situ in said cell, while sensing in situ in said siphon cell a parameter of the liquid sample as said reaction with said reagent proceeds.

2. The titration method of claim 1 wherein said sample is taken directly from the liquid process stream of an industrial lant, the pressure of said stream serving to produce said flow of process liquid through said inlet conduit means into said cell and into said drain/siphon conduit.

* * * * *

UNITED STATES PATENT AND TRADEMARK OFFICE
CERTIFICATE OF CORRECTION

PATENT NO. : 4,910,151

DATED : March 20, 1990

INVENTOR(S) : Moses Platt

It is certified that error appears in the above-identified patent and that said Letters Patent is hereby corrected as shown below:

In the Abstract:
  line 7, insert --.-- after "inlet";
  line 7, "negative" should be "Negative--;

Col. 2, line 21, "example" should be --sample--;
Col. 2, line 23, "mens" should be --means--;
Col. 2, line 59, "mean" should be --means--;
Col. 2, line 67, "te" should be --the--;

Col. 3, line 22, "ssed" should be --used--;
Col. 3, line 60, "settion" should be --section--;

Col. 4, line 3, "titran" should be --titrant--;
Col. 4, line 37, "elected" should be --selected--;
Col. 4, line 49, "sandard" should be --standard--;

Col. 5, line 36, "form" should be --from--;
Col. 5, line 40, "8m," should be --8ml--;
Col. 5, line 44, "thenoopened" should be --then opened--;
Col. 5, line 47, "i" should be --in--;
Col. 5, line 52, "redetermined" should be --predetermined--;

Col. 6, line 18, "mutt" should be --must--;
Col. 6, line 59, "aove" should be --above--;
Col. 6, line 65, "losed" should be --closed--;

UNITED STATES PATENT AND TRADEMARK OFFICE
CERTIFICATE OF CORRECTION

PATENT NO. : 4,910,151
DATED : March 20, 1990
INVENTOR(S) : Moses Platt

It is certified that error appears in the above-identified patent and that said Letters Patent is hereby corrected as shown below:

Col. 7, line 45, "oo" should be --to--;

Col. 8, line 20, "aid" should be --said--;
Col. 8, line 48, "proressively" should be --progressively--;
Col. 8, line 56, "lant" should be --plant--.

Signed and Sealed this

Fourth Day of June, 1991

*Attest:*

HARRY F. MANBECK, JR.

*Attesting Officer*      *Commissioner of Patents and Trademarks*